US005545720A

United States Patent [19]
Koyama et al.

[11] Patent Number: 5,545,720
[45] Date of Patent: Aug. 13, 1996

[54] PROTEIN PHBP-70

[75] Inventors: Masayoshi Koyama; Mikiko Takahashi, both of Saitama; Kazuyuki Doi, Tokyo, all of Japan

[73] Assignee: Hoechst Japan Limited, Tokyo, Japan

[21] Appl. No.: 414,427

[22] Filed: Mar. 31, 1995

[30] Foreign Application Priority Data

Mar. 31, 1994 [JP] Japan .................................. 6-061905

[51] Int. Cl.[6] .................... A61K 35/14; A61K 38/18; A61K 38/16; C07K 14/475
[52] U.S. Cl. ................... 530/380; 530/350; 530/399
[58] Field of Search ......................... 530/350, 413, 530/399, 418, 419, 420, 829, 830, 380; 514/12, 21

[56] References Cited

U.S. PATENT DOCUMENTS 5,166,317  11/1992  Wallace et al. ................... 530/350
5,227,302  7/1993  Heldin et al. ..................... 435/240.2

OTHER PUBLICATIONS

Casscells et al. "Isolation, Characterization, & Localization of Heparin–Binding Growth Factors In The Head" J Clin Invest. 85 433–441 1990.
Marikovsky et al. "Appearance of Heparin–Binding EhF–life growth Factor In Wound Fluid as a Response To Injury" Proc Natl Acad Sci. go 3889–3893 1993.

Primary Examiner—Christina Y. Chan
Assistant Examiner—Nancy J. Degen
Attorney, Agent, or Firm—Foley & Lardner

[57] ABSTRACT

A protein named PHBP-70 having a wound-healing activity which has a molecular weight of about 60–80 KDa by analysis with SDS-PAGE under reducing conditions and can be obtained from the blood of the fetus and neonates of mammals including human beings. The protein PHBP-70 is a novel protein having a fibroblast proliferating activity and thus it is useful as a wound-healing agent.

4 Claims, 5 Drawing Sheets

PROTEIN PHBP-70

BACKGROUND OF THE INVENTION

1. Field of the Invention

This invention relates to a novel protein, more particularly, to a protein having a heparin-binding property and a fibroblast proliferating activity. The protein of this invention is named PHBP-70 (Plasma Heparin Binding Protein-70) and can be obtained from the blood of mammals including human beings.

2. Description of the Prior Art

Various growth factors are known to be involved in the course of wound healing (Dijke et al., Biotechnology, vol. 7, p. 793–798, 1989). Particularly, TGF-β (transforming growth factor-β) and PDGF (platelet-derived growth factor) are known to proliferate fibroblast, induce the cells to the site of lesions and promote repairing wounds. However, it has not been reported yet that the substance of the present invention enhances proliferation of fibroblast and is effective for wound healing.

DETAILED DESCRIPTION OF THE INVENTION

Thus, an object of the invention is to provide a novel protein which can be used as a therapeutic agent effective for wound healing.

It is considered that, in the blood of mammals including human being, are contained the various growth factors which stimulate growth of cell tissues of the mammals. Bovine plasma which is easily available in quantity was used as a starting material for purification and isolation of a novel protein having a fibroblast proliferating activity. For example, the strain of the cell, Balb/3T3, can be used for determination of fibroblast proliferating activity.

Firstly, barium chloride was added to the plasma to obtain calcium binding protein adsorbed on barium. A fraction containing said proteins was then subjected to an anion column chromatography to remove a blood coagulation factor binding to the column. The flow-through fractions were subjected to heparin affinity column chromatography to isolate fractions binding to the column, since various growth factors were known to bind heparin. The fractions were further purified by gel filtration column, anion column chromatography and reverse-phase liquid chromatography. These fractions were determined for fibroblast proliferating activity. Each active fraction thus obtained was determined for the N-terminal amino acid sequence and amino acid composition, and was investigated referring to the protein and gene data base whether or not any known proteins are found. As a result, a fraction was found to be a novel protein.

The protein was named PHBP-70.

The protein PHBP-70 provided according to the invention is a novel protein isolated from animal blood, having the following physical properties and N-terminal amino acid sequence.

1) Molecular weight: About 60–80 KDa (by SDS-PAGE method under reducing condition)

2) N-terminal amino acid sequence: Amino acid sequence shown in SEQ ID No.:1 of the Sequence Listing 3) Character: Having a heparin binding property and a fibroblast proliferating activity PHBP-70 is expected to be a protein which would be more suitable for preparations by some modification of amino acid residues and chemical modification or fragmentation, without losing a fibroblast proliferating activity.

PHBP-70 is highly water soluble and is most suitably administered for wound healing in combination with an appropriate water soluble base preferably by applying directly to an affected region. In addition, it can be administered systemically as intravenous injections or hypodermic preparations, and nasally or transpulmonarily as fine-grain aerosol preparations.

The dosages are 1–100 μg/administration site/person/day in local administration and 0.1–10 mg/kg/day in systemic administration.

The following examples are intended to further illustrate the invention and are not to be construed to limit the invention.

EXAMPLE 1

Purification of Fibroblast (Balb/3T3 Cells) Proliferation Promoting Factor from Bovine Plasma 1) Removal of Vitamin K-dependent Protein from Bovine Plasma To 19 lit. of bovine plasma was added 1 lit. of anticoagulant (3.8% sodium citrate, 10 mM benzamidine-HCl) and mixed well. To the mixture was added 2 lit. of 1M barium chloride at 4° C. while stirring and then the resulting mixture was allowed to stand for one hour. A white precipitate was collected by centrifugation (4000 rpm, 5 minutes), washed with sodium chloride containing 3 mm benzamidine-HCl, 0.01M barium chloride and 0.02% sodium azide and then centrifuged to obtain the precipitate. This procedure was repeated twice.

To the precipitate was added 1.5 lit. of 40% saturated ammonium sulfate (pH 7.0) and the mixture was allowed to stand at 4° C. overnight while stirring. After the precipitate was removed by centrifugation (4000 rpm, 30 minutes), solid ammonium sulfate was added to the supernatant to give 70% saturation, allowed to stand for an hour and centrifuged (4000 rpm, 30 minutes). The precipitate was dissolved in 100 ml of phosphate buffer A (0.05M sodium phosphate, 0.2M sodium chloride, 1 mM benzamidine-HCl, 0.02% sodium azide, pH 6.0) and dialyzed against the same buffer. After completion of the dialysis, the supernatant was obtained by centrifugation (15,000 rpm, 30 minutes) [Hashimoto, N., et al., J. Biochem. (1985), Vol. 97, p. 1347–1355]. The supernatant was developed in a DEAE-Sepharose CL-6B column (a column size of a diameter 5 cm×a length 30 cm), which had been pre-equilibrated with the same buffer, to remove the vitamin K-dependent proteins by adsorption, thereby obtaining the fraction passing therethrough.

2) Partial Purification by Heparin Affinity Column Chromatography, Gel Filtration Column and Anion Column Chromatography The fraction was developed in heparin-Sepharose CL-6B column (a diameter 1.6 cm×a length 15 cm, Pharmacia AB), which had been pre-equilibrated with the phosphate buffer A, at a low rate of 1 ml/minute. The column was thoroughly washed with the phosphate buffer A.

After washing, the peptides or proteins adsorbed on the heparin-Sepharose CL-6B column were eluted with a linear gradient of 0.2–1.5M sodium chloride. The eluate was monitored with absorbance at 280 nm using a spectrophotometer. The elution pattern is shown in FIG. 1. The active fraction of about 120 ml was collected. Thereafter, the fraction was concentrated using Filtron ultrafilter and the concentrate was applied onto Sephacryl S-200HR gel filtration column (a diameter 2.6 cm×a length 92 cm, Pharmacia AB), which had been pre-equilibrated with Tris buffer (20 mM tris-HCl, 0.1M sodium chloride, pH 8.0), and then development was performed at a flow rate of 1 ml/minute.

The eluate was monitored with absorbance at 280 nm using a spectrophotometer. The active first peak of about 51 ml was collected. The elution pattern is shown in FIG. 2. Next, a portion of the fraction was developed in Mono Q column (a diameter 0.5 cm×a length 10 cm, Pharmacia AB), which had been pre-equilibrated with the said Tris buffer. After washing with the Tris buffer, elution was performed with a linear gradient of 0.1–1.0M sodium chloride. The eluate was monitored with absorbance at 280 nm using a spectrophotometer. The active fraction of about 8 ml was collected. The elution pattern is shown in FIG. 3.

3Purification by Reverse Phase HPLC

The eluate obtained according to the above procedure 2) was developed over a Cosmosil 5C$_{18-300}$ column (a diameter 4.6 mm×a length 250 mm, available from NACALAI TESQUE INC.), which had been pre-equilibrated with 10% acetonitrile containing 0.1% trifluoroacetic acid (TFA), and then the column was thoroughly washed with the same solution. Then, the peptides or proteins adsorbed were eluted with a linear gradient of 10–70% acetonitrile. The eluate was monitored with absorbance at 214 nm to collect the fraction at every peak. Active peaks (arrow-marked) were collected. The elution pattern is shown in FIG. 4.

EXAMPLE 2

Determination of Fibroblast Proliferation Promoting Activity

Fibroblast cell strain, Balb/3T3 cells (purchased from ATCC, Catalogue No. CCL163 Balb/3T3-clone A31) were inoculated into a 96-well culture plate at 5×10$^3$ cells/well and 100 μl of 10% calf serum-containing Dulbecco Modified Eagle Medium (hereinafter referred to as DME) was added and cultured in an incubator at 37° C. for 24 hours. The culture medium was then removed and after the cells were washed, 100 μl of a lowered serum medium (0.2% calf serum-containing DME) was added to the wells and incubation was continued for further 3 days. Ten μl each of the fractions obtained in Example 1 were added thereto and incubation was performed for 15 hours. Then, $^3$H-thymidine was added to be 74 KBq/ml and incubation was performed for 6 hours. After completion of the incubation, the cells were collected and the amount of $^3$H-thymidine incorporated in the cells was determined.

As a result, a cell proliferation promoting activity was observed in the fraction with the Peak 1 (arrow-marked) in FIG. 4.

EXAMPLE 3

Determination of Physico-chemical Properties of the Peptide at the Peak 1

1) Analysis for the N-terminal Amino Acid Sequence

The peptide in the fraction, the activity of which was confirmed in Example 2, was analyzed for the N-terminal amino acid sequence using an amino acid sequencer, model 477A (available from Applied Biosystems Inc.) to determine the amino acid sequence as shown in SEQ ID No.:1 in the Sequence Listing. This sequence was investigated upon protein data base whether or not there may be found any corresponding one to confirm that it is a novel protein.

2) Amino Acid Composition Analysis

The amino acid composition of the peptide at the Peak 1 was investigated using an amino acid analyzer. The result of the amino acid composition analysis is shown in Table 1.

TABLE 1

| Amino acid | Analysis results (*1) |
|---|---|
| Asp | 60.3 (60) |
| Glu | 81.2 (81) |
| Ser | 35.6 (36) |
| Gly | 36.5 (37) |
| His | 16.7 (17) |
| Arg | 42.0 (42) |
| Thr | 43.7 (44) |
| Ala | 41.1 (41) |
| Pro | 35.2 (35) |
| Tyr | 18.9 (19) |
| Val | 37.7 (38) |
| Met | 12.9 (13) |
| Cys$_{/2}$ | N.D. (*2) |
| Ile | 18.8 (19) |
| Leu | 75.6 (76) |
| Phe | 32.3 (32) |
| Lys | 42.2 (42) |
| Trp | N.D. (*2) |

(*1) Calculated in terms of the molecular weight of 70,000 Dalton
(*2) Not determined 3Analysis Using Electrophoresis The molecular weight of the peptide at the Peak 1 was estimated with SDS-PAGE under reducing conditions to show a molecular weight of about 60–80 KDa (FIG. 5). The lane 1 in FIG. 5 shows a band of the peptide at the Peak 1 and the lane 2 shows a molecular weight marker.

In consideration of the results as shown in the above examples 1), 2) and 3), it was confirmed that the peptide at the Peak 1 having a fibroblast proliferating activity is a novel protein.

EXAMPLE 4

Determination of Fibroblast Proliferating Activity of PHBP-70

In order to further investigate a dose-dependent cell proliferation promoting activity of PHBP-70 obtained in Example 2, PHBP-70 was added to the same culture plate at 0.3–10 μg/ml per well according to the same procedure as described in Example 2, and incorporation of $^3$H-thymidine was determined.

The results of the determination of fibroblast proliferating activity of PHBP-70 are shown in Table 2, wherein the data show the mean and its standard deviation (4 cases per one group).

TABLE 2

| Added Compound | Dose (μg/ml) | Incorporated $^3$H-thymidine (cpm) |
|---|---|---|
| Control | — | 437.4 ± 57.4 |
| PHBP-70 | 0.3 | 434.6 ± 13.1 |
|  | 1.0 | 467.4 ± 44.3 |
|  | 3.0 | 1670.3 ± 81.9 |
|  | 10.0 | 6356.9 ± 68.1 |

It was confirmed that PHBP-70 has a dose-dependent cell proliferation promoting activity by the results.

The protein PHBP-70 provided according to the present invention has a fibroblast proliferation promoting activity and then it is useful as a wound-healing agent.

Figure 1:
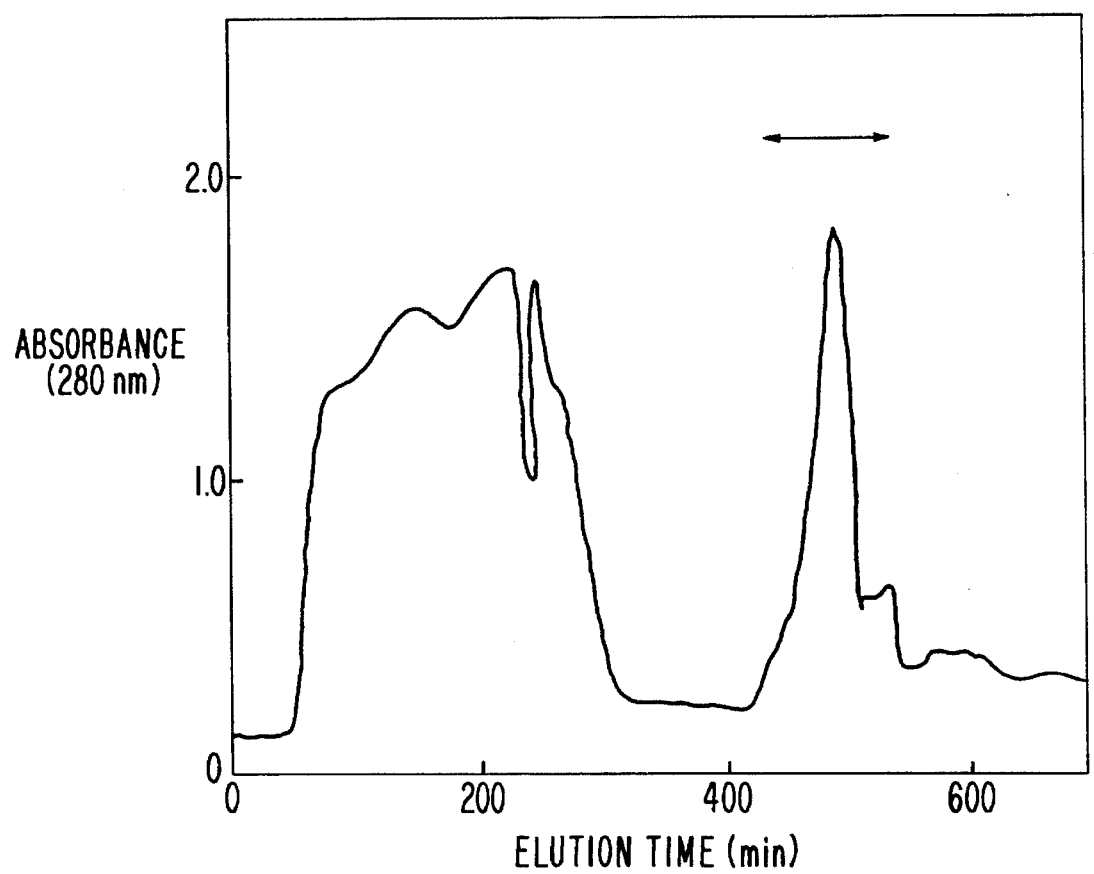
FIG. 1 shows an elution pattern of the fractions developed by heparin affinity column chromatography. The arrow mark shows the active fractions containing the protein.
Figure 2:
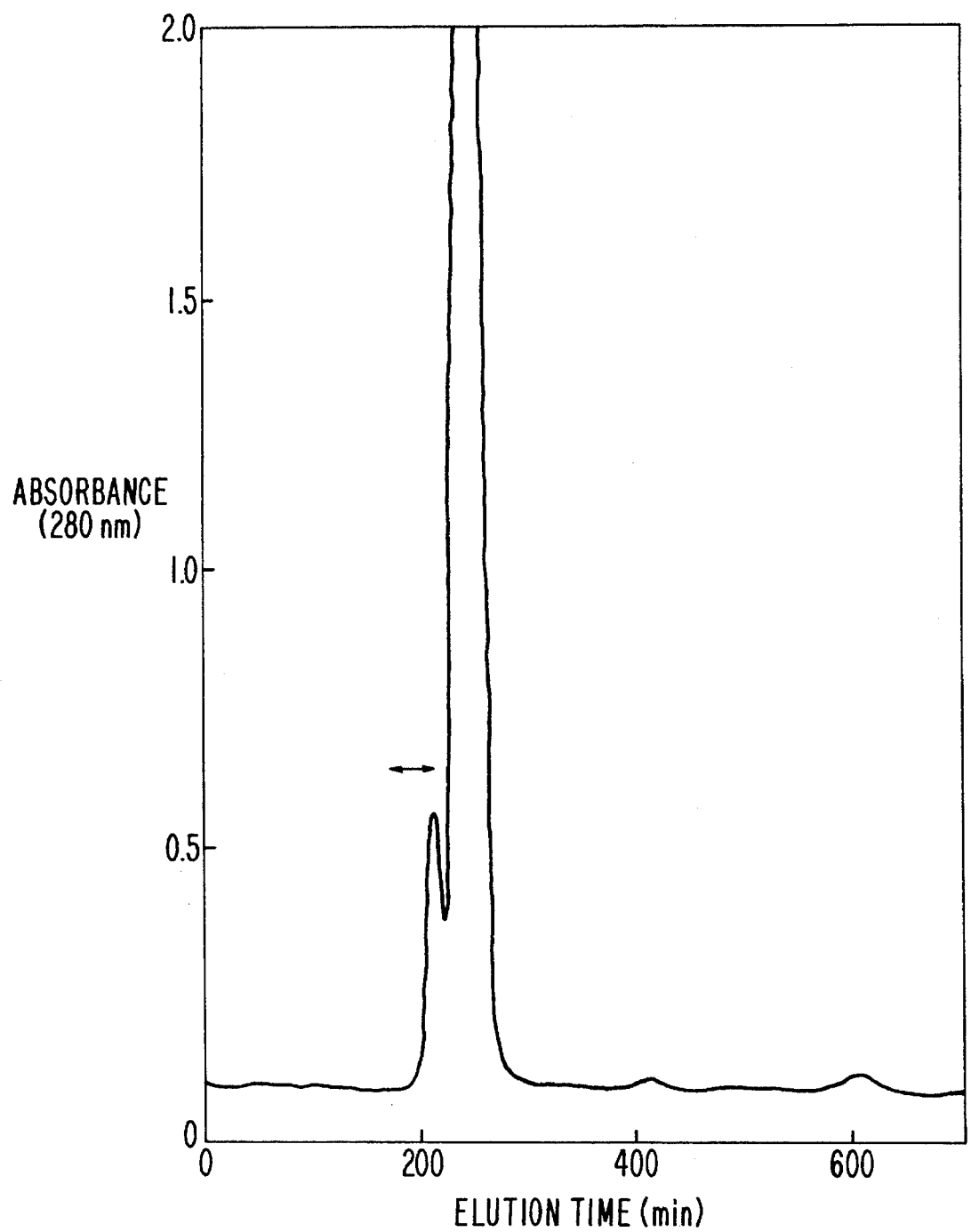
FIG. 2 shows an elution pattern of Sephacryl S-200HR gel filtration monitored with absorbance at 280 nm using a spectrophotometer.
Figure 3:
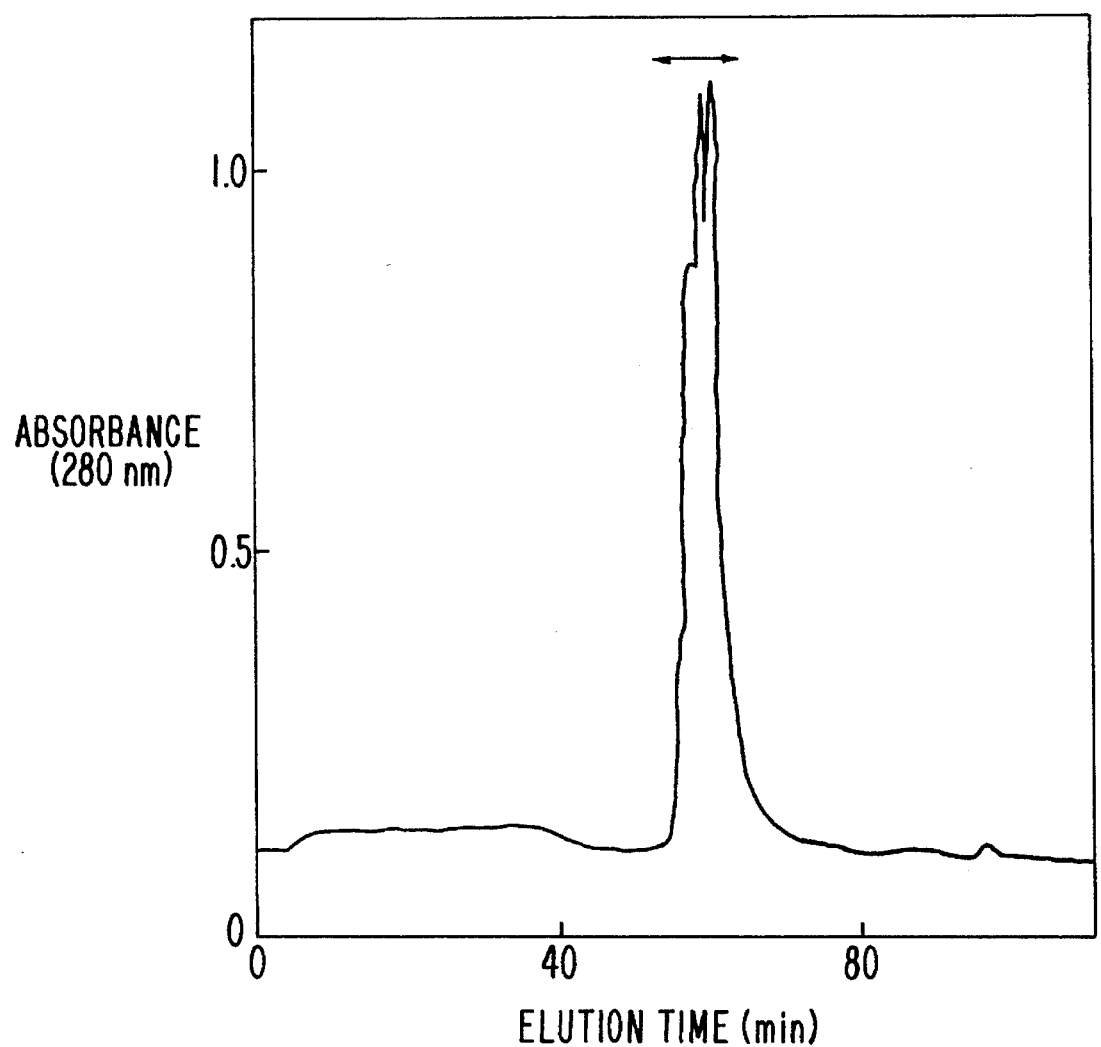
FIG. 3 shows an elution pattern of Mono Q column monitored with absorbance at 280 nm using a spectrophotometer. The elution has been performed with a linear gradient of 0.1–1.0M sodium chloride.
Figure 4:
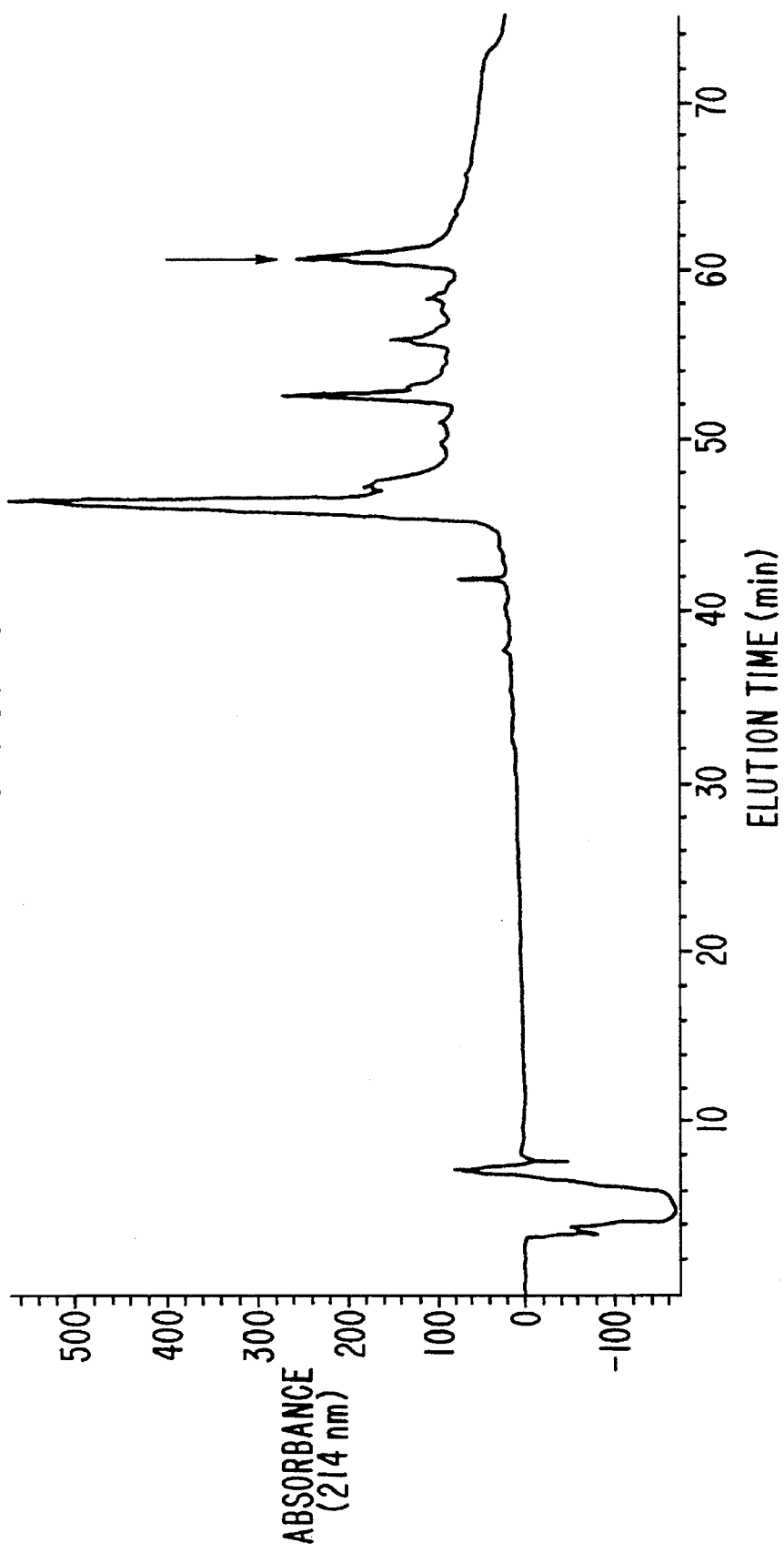
FIG. 4 shows an elution pattern of $5C_{18-300}$ monitored with absorbance at 214 nm using a spectrophotometer. The elution has been performed with a linear gradient of 10–70% acetonitrile.
Figure 5:
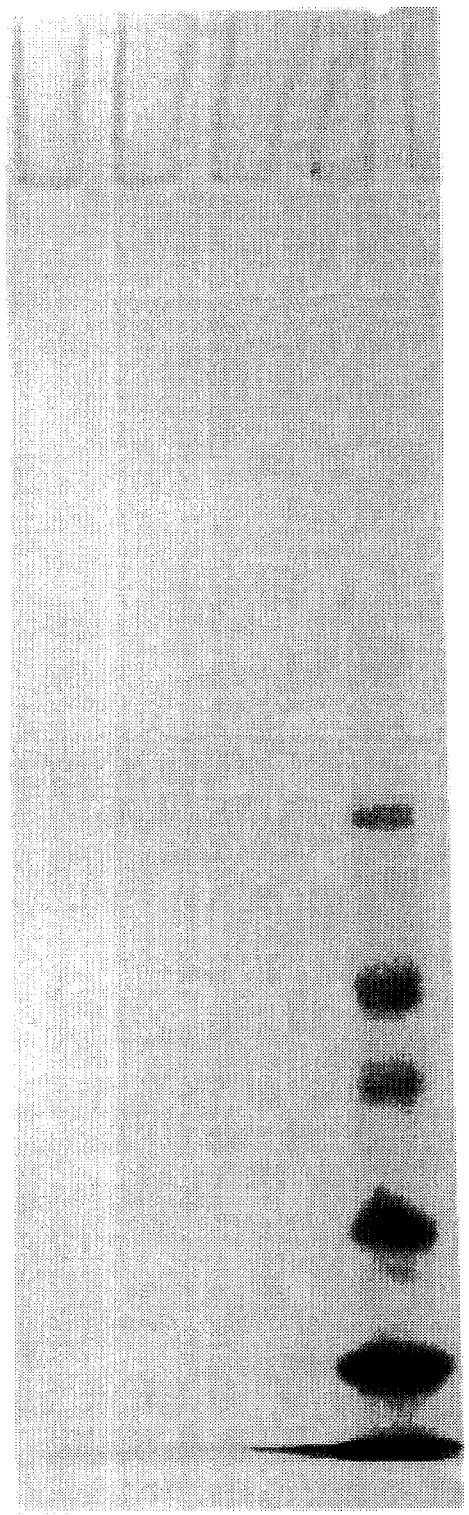
FIG. 5 shows an electrophoresis pattern of the peptide at the Peak 1.

protein-70 (PHBP-70) having a molecular weight of about 60–80 KDa by analysis with SDS-PAGE under reducing conditions and having the N-terminal amino acid sequence described in SEQ ID No.:1 of the Sequence Listing.

2. The protein PHBP-70 as claimed in claim 1 isolated from mammalian blood.

3. The protein PHBP-70 as claimed in claim 1 wherein said protein is a heparin binding growth factor.

4. A wound healing agent comprising an effective amount of the isolated protein PHBP-70 of claim 1.

---

---

What is claimed is:

1. An isolated protein named plasma heparin binding

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION SEQ ID NO:1:

```
Ser Met Ser Pro Glu Ala Gln Ala Gly Leu Glu Thr Leu Leu Thr Pro
1               5                   10                  15
Met
```